United States Patent [19]

Oshefsky et al.

[11] Patent Number: 4,578,133
[45] Date of Patent: Mar. 25, 1986

[54] METHOD AND APPARATUS FOR APPLYING DISCRETE STRIPS TO A WEB OF MATERIAL

[75] Inventors: Daniel J. Oshefsky; Paul A. Gavronski; Robert E. Vogt; Gregory J. Rajala, all of Winnebago County, Wis.

[73] Assignee: Kimberly-Clark Corporation, Neenah, Wis.

[21] Appl. No.: 673,064

[22] Filed: Nov. 19, 1984

[51] Int. Cl.$^4$ ............... B29H 15/00; B60C 29/00; B44C 1/16; B32B 31/00

[52] U.S. Cl. ............... 156/164; 156/214; 156/230; 156/232; 156/244.18; 156/246; 156/300; 156/265; 264/295

[58] Field of Search ............... 156/163, 164, 264, 265, 156/229, 300, 230, 231, 232, 201, 212, 214, 244.18, 246, 249, 297, 303; 264/259, 285, 297.5, 294, 295, 320, 339

[56] References Cited

U.S. PATENT DOCUMENTS

| | | | |
|---|---|---|---|
| 3,524,781 | 8/1970 | Winterroth et al. | 156/232 |
| 3,728,191 | 4/1973 | Wierzba et al. | 156/265 |
| 3,994,767 | 11/1976 | Smith | 264/295 |
| 4,208,363 | 6/1980 | Yevick | 264/295 |
| 4,227,952 | 10/1980 | Sabee | 156/164 |
| 4,284,454 | 8/1981 | Joa | 156/229 |
| 4,293,367 | 10/1981 | Klasek et al. | 156/164 |
| 4,297,157 | 10/1981 | Van Vliet | 156/229 |
| 4,352,712 | 10/1982 | Paul | 156/230 |

*Primary Examiner*—Edward Kimlin
*Assistant Examiner*—L. Felasco

[57] ABSTRACT

Continuous strips of a first material, e.g., elastic strips, are continuously supplied to flexible strip supports in a supply zone while the strip supports are in a linear configuration. The strip supports are carried on respective transfer members which are mounted on a rotatable support so that individual transfer members follow a closed (orbital) path upon rotation of the support. The continuous strips are cut into discrete strips adhered to respective flexible strip supports whose configuration, and that of the discrete strips adhered thereto, is then changed to a desired curvilinear configuration. The transfer members are then brought into transfer contact in a transfer zone with a moving web of second material, which may comprise the backing sheet of a disposable diaper construction, and the curvilinear strips are transferred to the web. Alternatively, or in addition, the individual transfer members are supported on radially translatable supports so that during rotation the orbital radius and thereby the linear velocity of individual transfer members may be selectively varied between a first radius and consequent linear velocity in the supply zone and a second radius and consequent linear velocity in the transfer zone. The individual transfer members may also be pivoted to selectively orient the strips relative to the moving web in the transfer zone. Apparatus to carry out the method provides a transfer means comprising a plurality of transfer members mounted for rotation on a rotatable member and preferably incorporating radially translatable supports for the individual transfer members, flexible strip supports of changeable configuration, and means to selectively pivot the individual transfer members.

19 Claims, 19 Drawing Figures

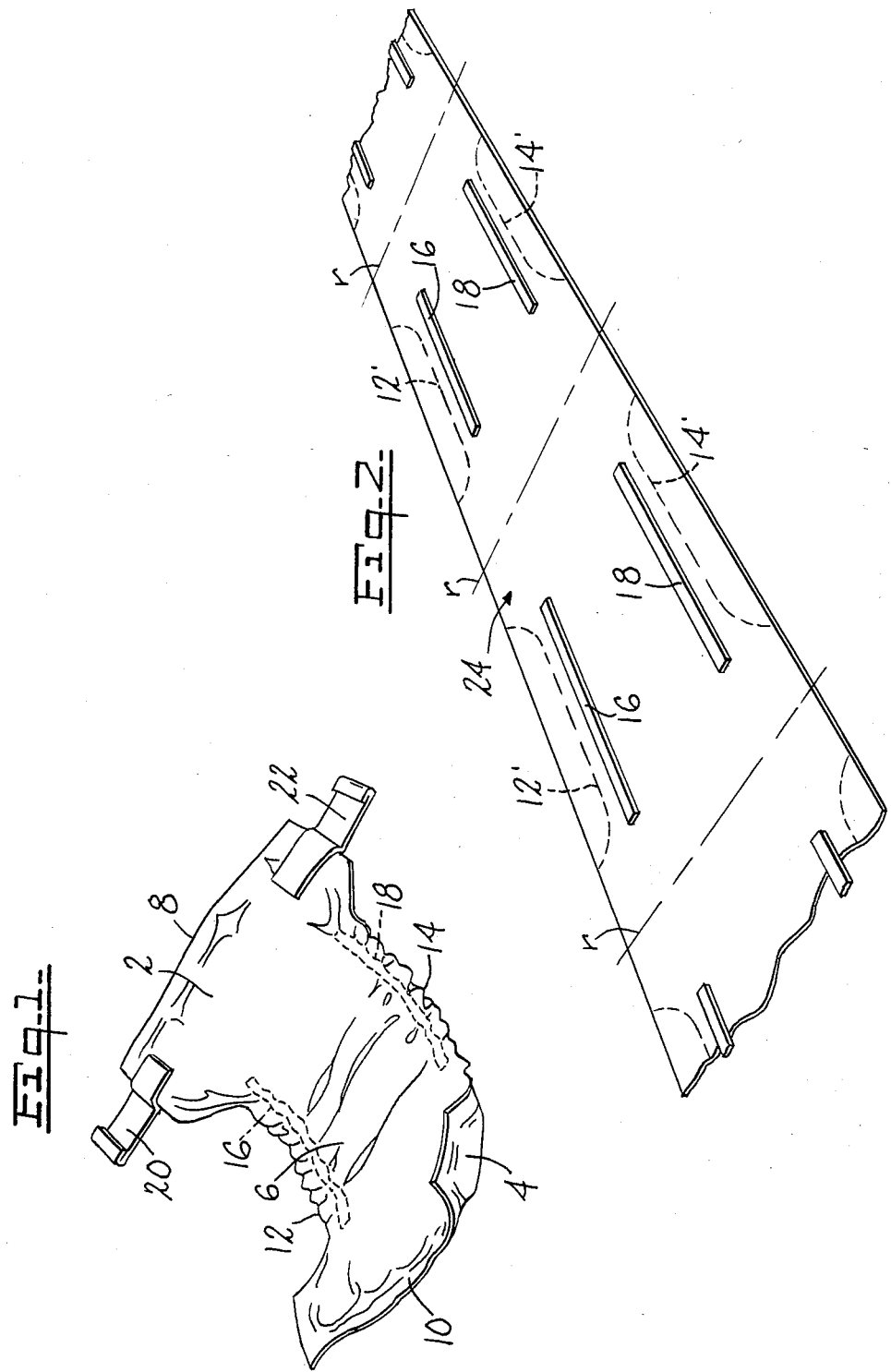

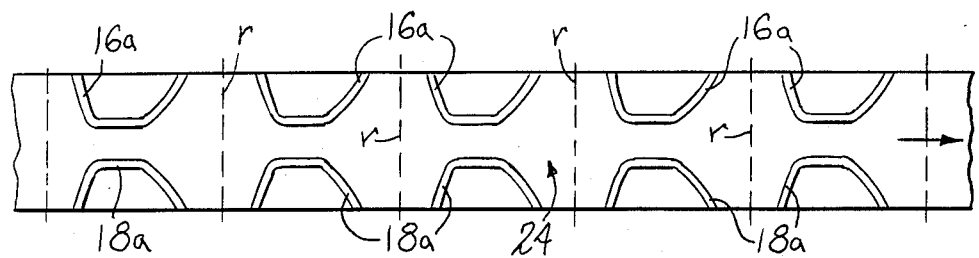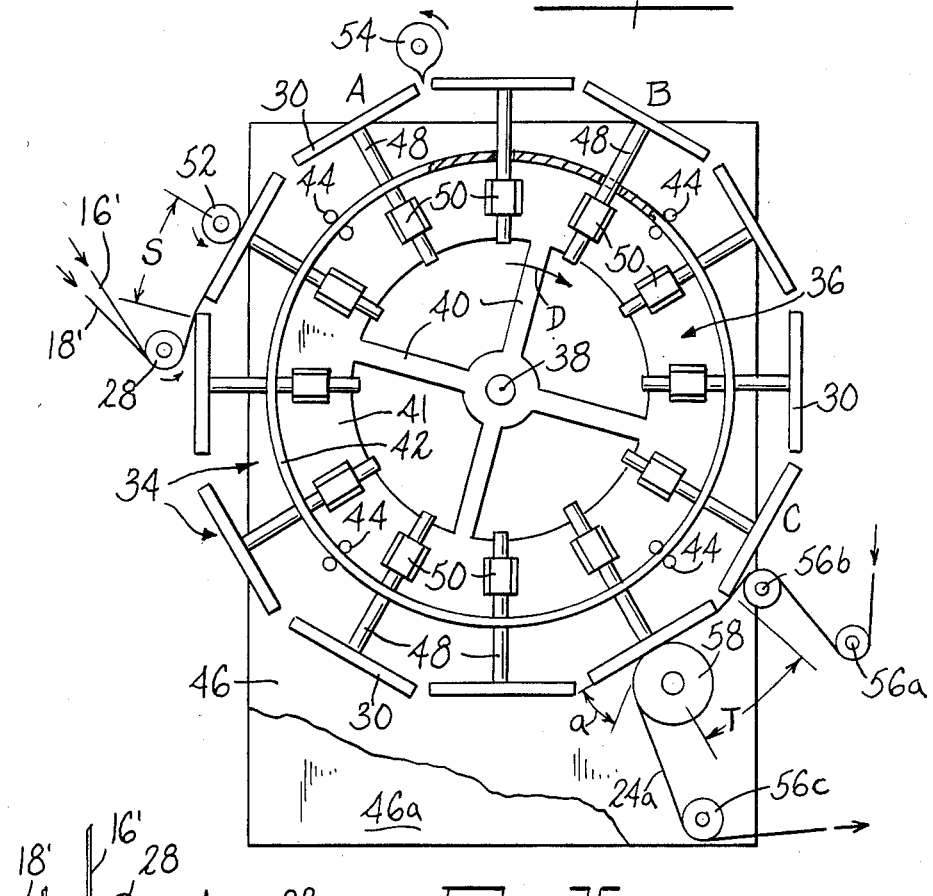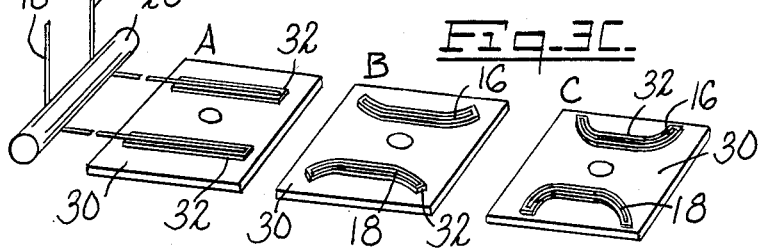

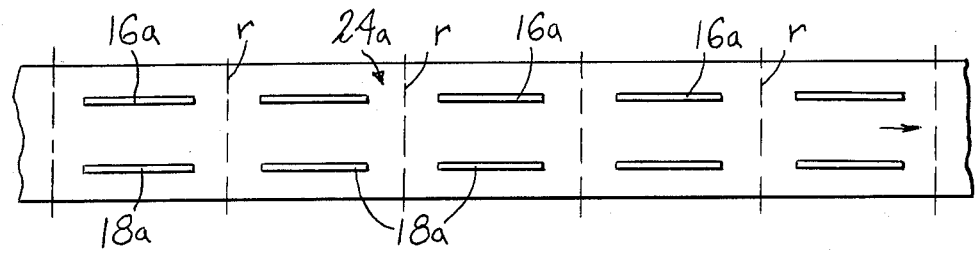
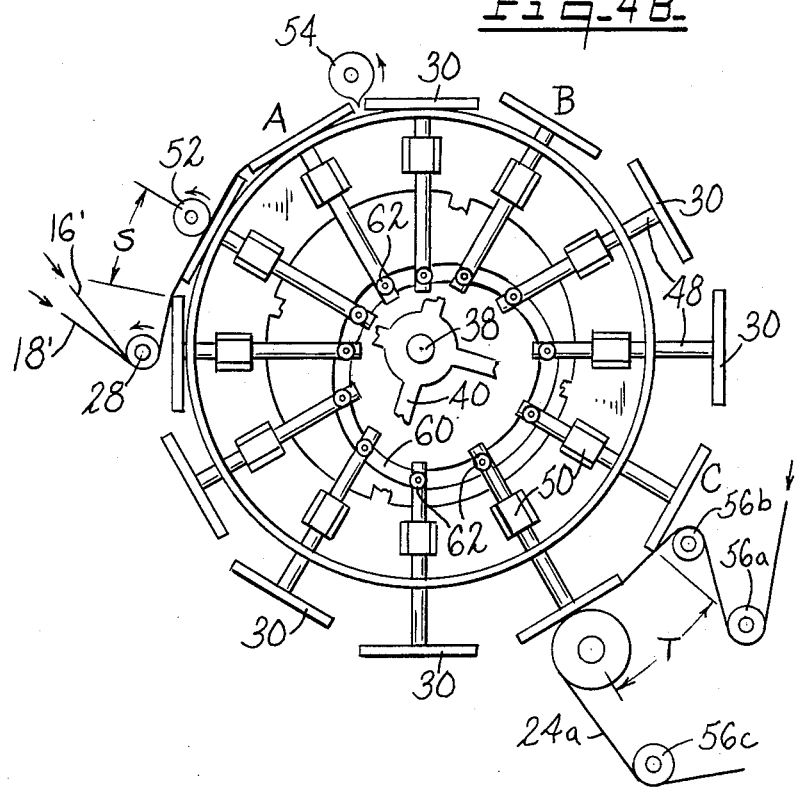
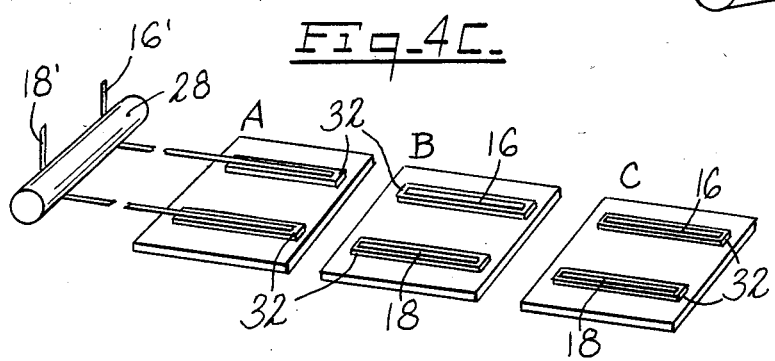

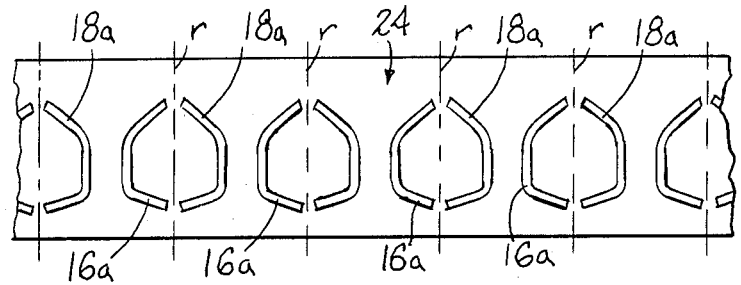
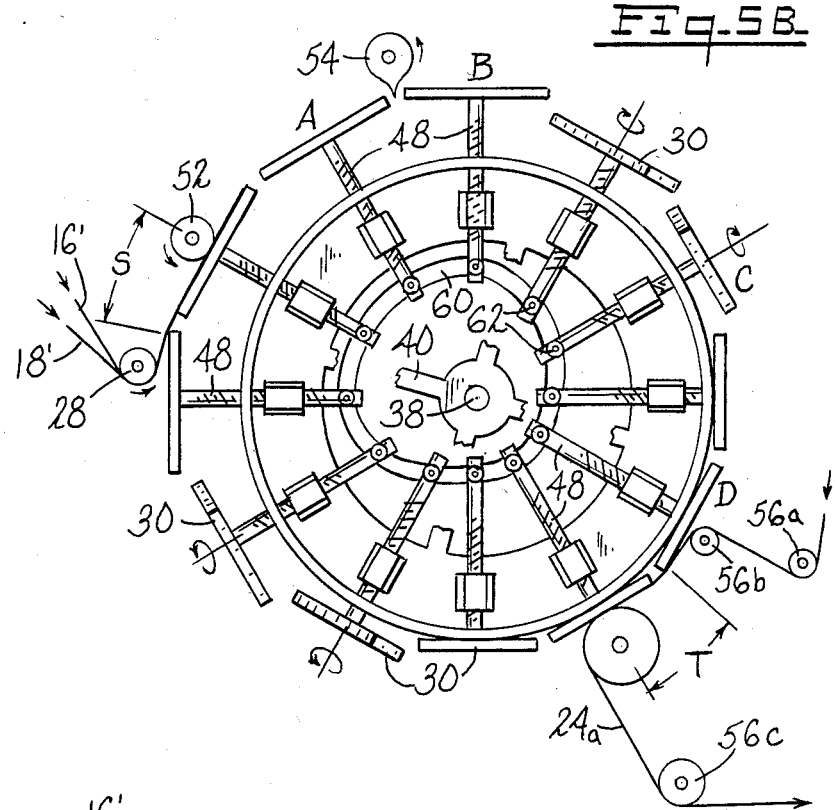
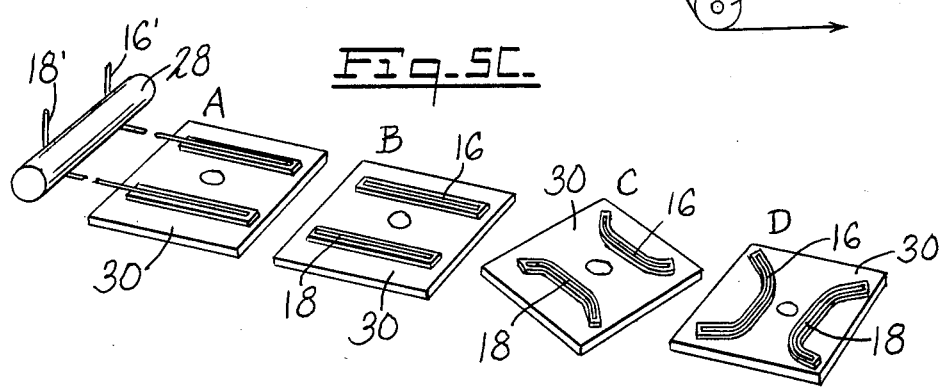

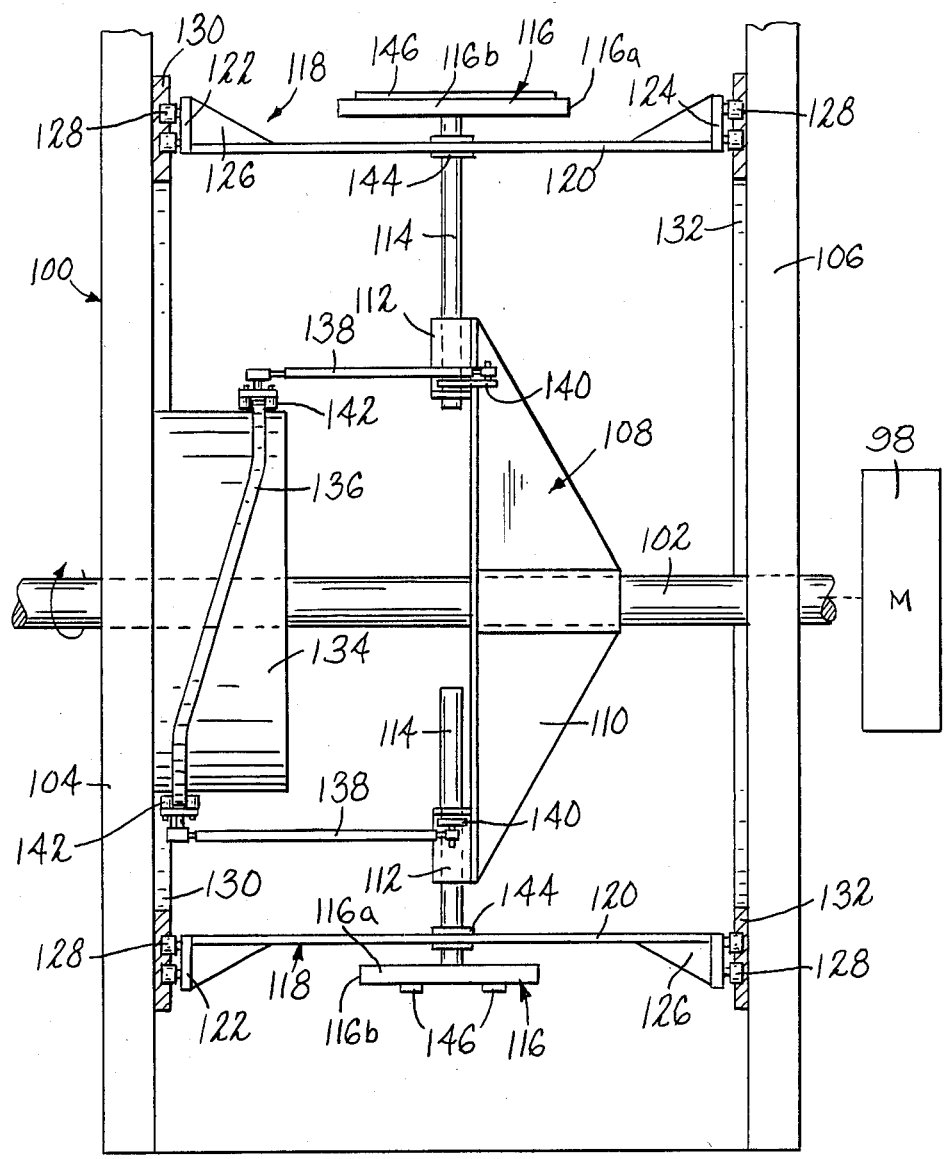

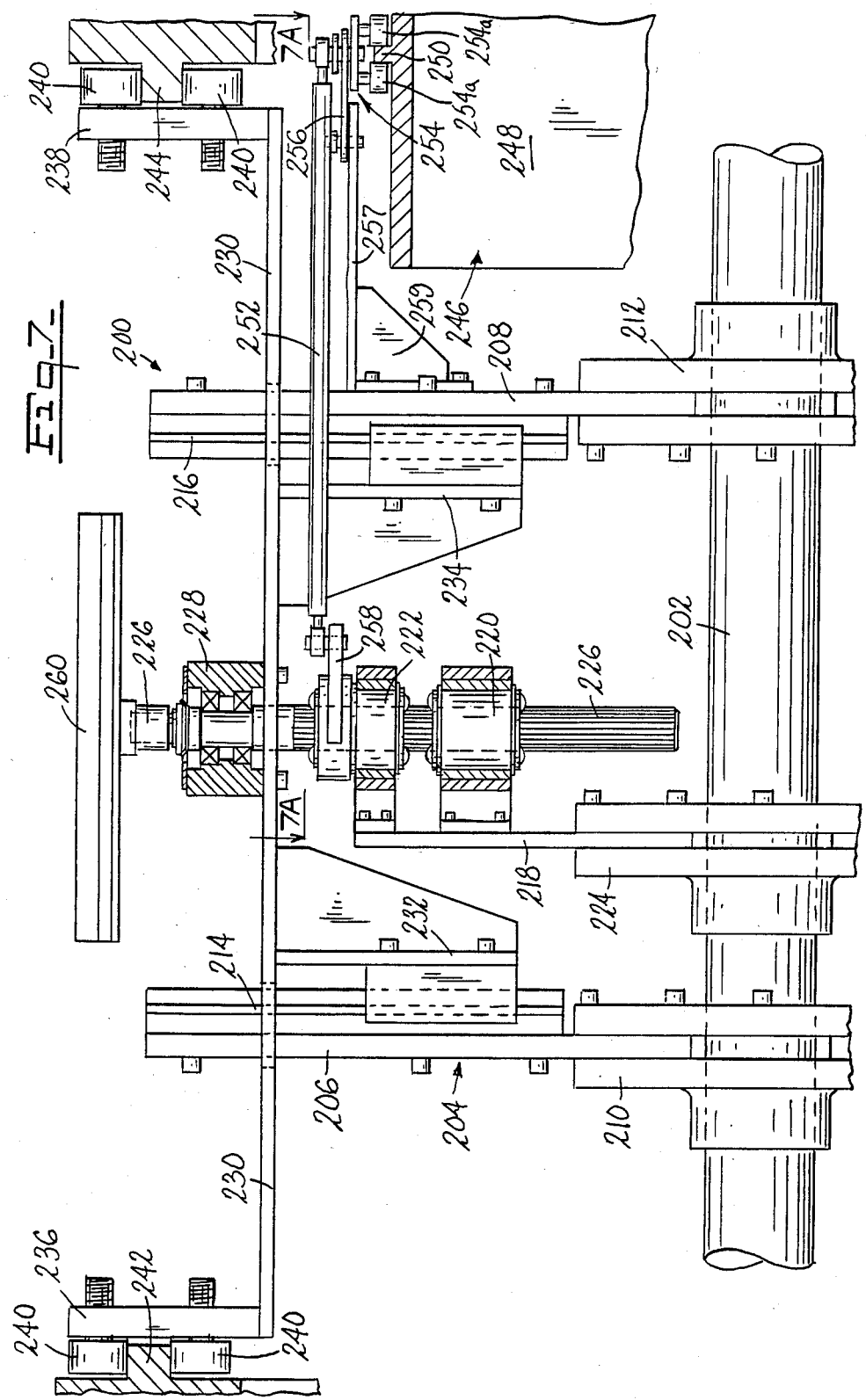

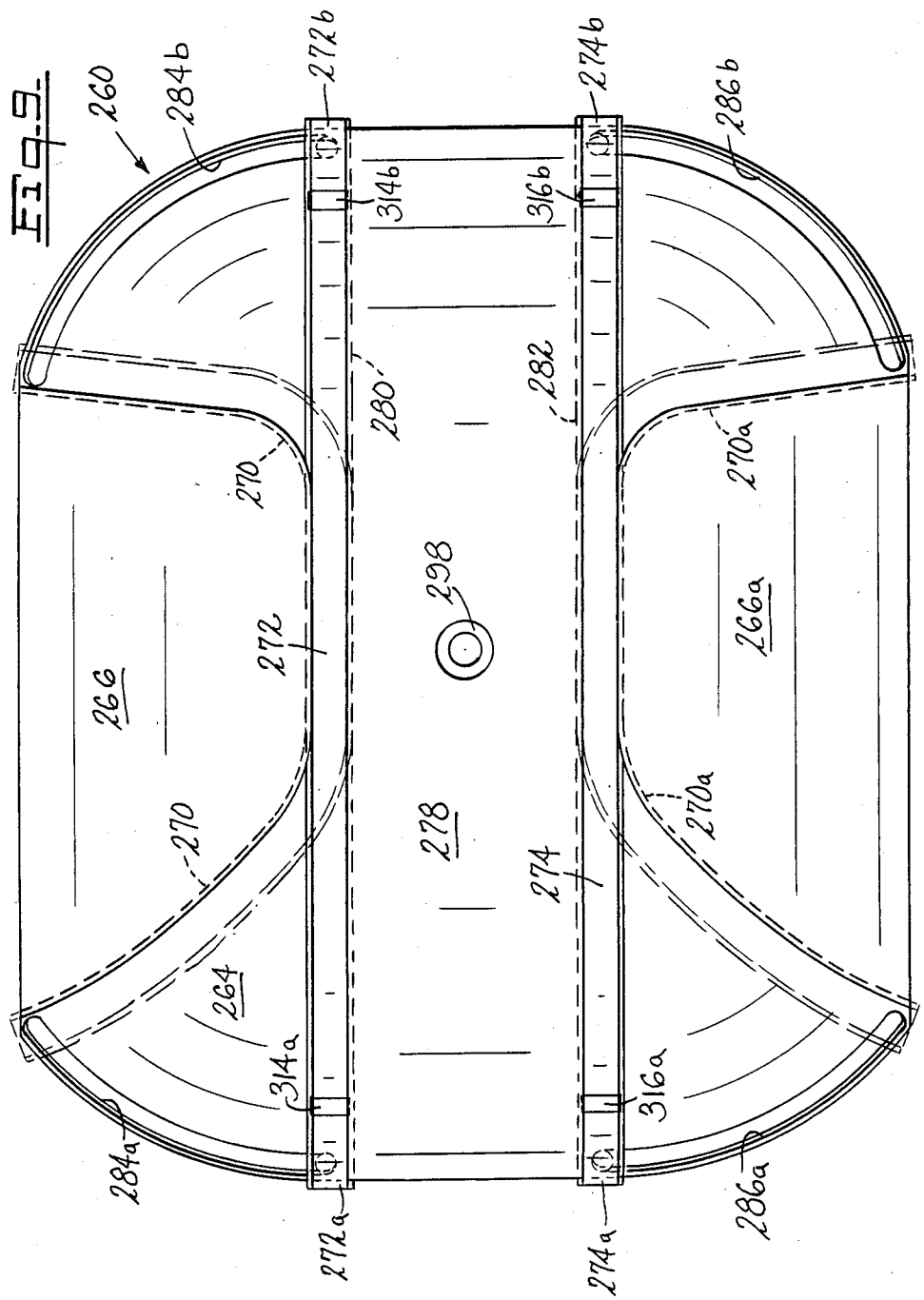

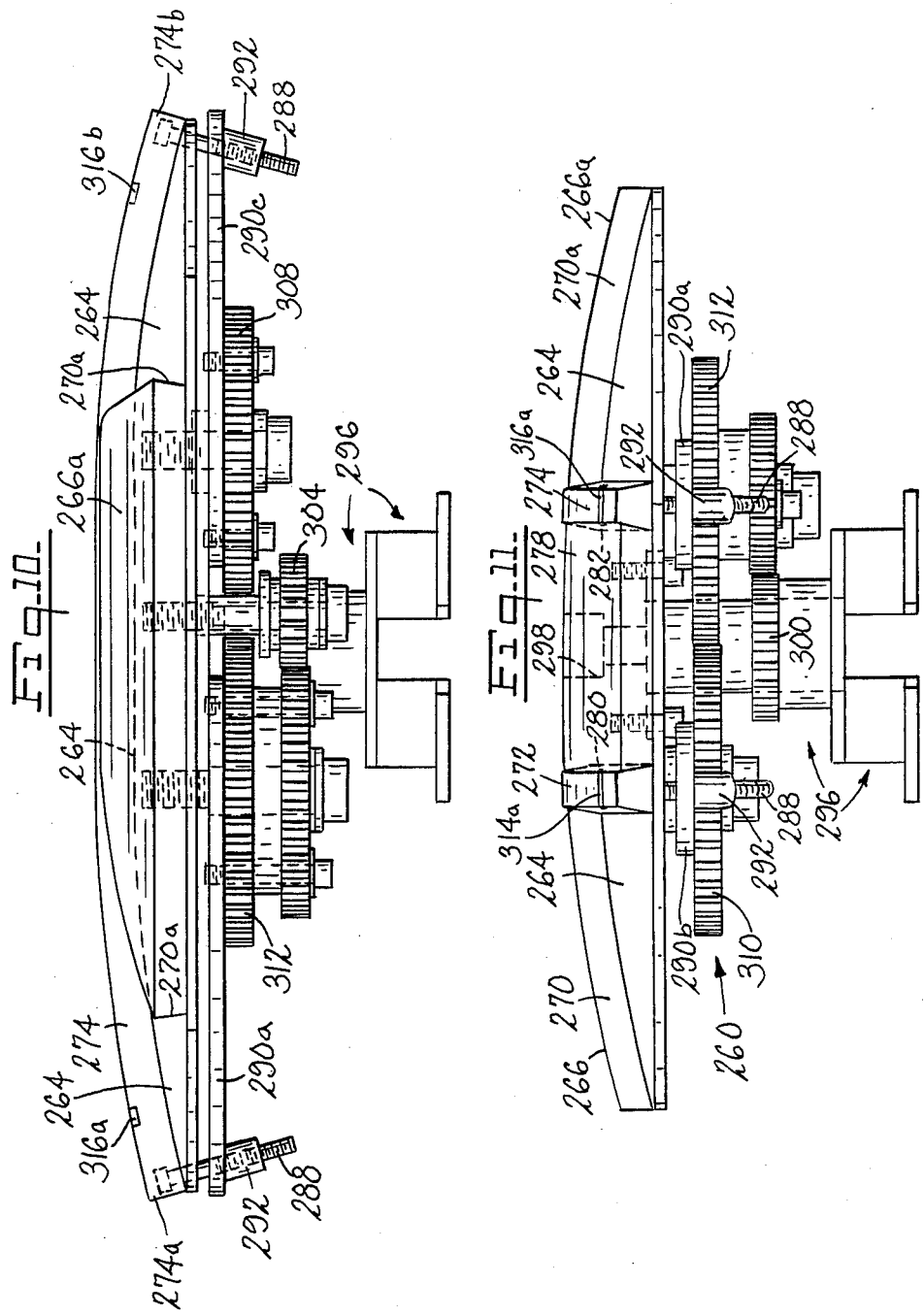

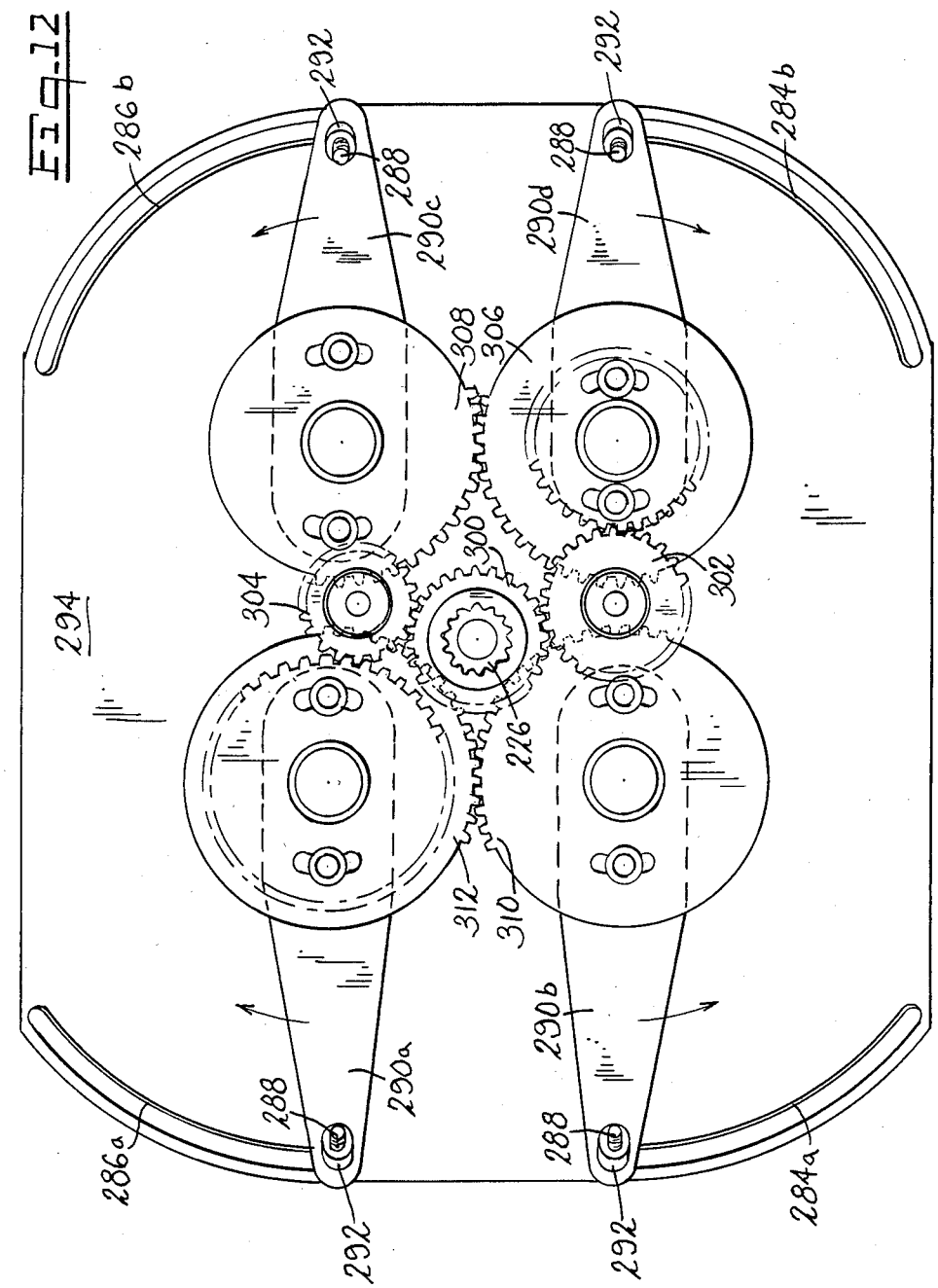

METHOD AND APPARATUS FOR APPLYING DISCRETE STRIPS TO A WEB OF MATERIAL

BACKGROUND OF THE INVENTION

The present invention is concerned with a method and apparatus for applying strips of one material to a web of second material and, more particularly, is concerned with a method and apparatus for applying elastic strips to a moving web of material. For example, the present invention has utility with respect to the application of elastic leg and/or waistband strips to a moving web of material which will be transversely cut into individual disposable diapers or other garments.

Generally, disposable diapers or the like are made with a fluid impervious backing sheet on which an absorbent sheet is (or individual absorbent pads are) positioned and covered by a liquid-pervious top sheet. The composite material is then cut into individual disposable diapers or the like. In the manufacture of such articles it is conventional practice to apply elastic strips to a moving web of backing sheet material to provide elastic sealing about the leg openings of the finished garment. In modern manufacturing of disposable diapers, the web or webs of material from which the diapers are made move at high speeds and consequently the accurate application of elastic strips of desired configuration to the rapidly moving web presents significant manufacturing problems. These problems are intensified when it is desired to apply the elastic strips in other than a straight linear configuration.

U.S. Pat. No. 4,227,952 is illustrative of the prior art expedient of forming transverse folds or tucks at spaced locations along the web of material and applying, by means of adhesive, a stretched elastic ribbon or strip longitudinally of the web and extending over the transverse tucks or folds. The elastic ribbon or strip is maintained in stretched condition until the adhesive sets and is then severed at the point where the elastic ribbon crosses the folds so that upon longitudinally straightening the web to remove the folds, spaced apart segments of elastic ribbon are formed thereon.

U.S. Pat. No. 4,284,454 illustrates a method and apparatus for applying elastic ribbon or strips transversely of a moving web of material by utilizing a first chain conveyor to position discrete elastic strips transversely of the moving web. A second set of transfer chains moving parallel to and in the same direction as the traveling web are used to pick up the discrete strips of elastic and apply them in their transversely oriented position to the moving web of material.

U.S. Pat. No. 4,297,157 discloses an applicator for placing elastic strips longitudinally on a moving web of material, the applicator comprising a series of movable and fixed clamps mounted on a main rotor body by means of radially extending connecting rods. The applicator receives a continuous strip or ribbon of elastic and cuts it into discrete lengths for longitudinal application of discrete linear strips of the elastic to the moving web of material.

U.S. Pat. No. 4,293,367 discloses means whereby strips of elastic may be applied to a moving web of material in a gently undulating pattern comprising straight, longitudinally extending segments and gently curved curvilinear segments. This is attained by utilizing an applicator head (illustrated in FIG. 5 of the patent) which is reciprocated transversely relative to the moving web of material and simultaneously pivoted. The reciprocating movement applies the strips in the undulating pattern and the pivoting maintains the axes of the elastic strip applicator rolls perpendicular to the line of deposition of the elastic strip during both the linear and curvilinear portions of the application cycle.

U.S. Pat. No. 3,728,191 shows a device for applying waistband tape to disposable diaper material in which applicators for the tape are mounted on a rotatable member and are radially pivotable to selectively orient the applied tape to the moving web as illustrated in FIG. 5 and described at column 5, lines 57 et seq. of the patent. The applicators are brought into contact with the moving web of material by the eccentric cam track arrangement illustrated in FIG. 5.

As mentioned above, the high linear speed of the moving web or webs of material used in modern manufacturing techniques increases the difficulty of oscillating or undulating the applied elastic web rapidly enough to attain sharp curvatures of the applied strip relative to the high speed moving web. In addition to requiring extremely high speeds of oscillation or rotation of the applicator heads, high mechanical stresses are set up in the moving web of material by such sharp direction changes of the applied strips. The web material, which is usually quite thin and of limited mechanical strength, may not be able to withstand such stresses without tearing.

SUMMARY OF THE INVENTION

In accordance with the present invention there is provided a method of applying discrete strips of a first material in a predetermined pattern to a web of a second material, the method comprising the following steps: supplying one or more discrete strips of the first material to one or more transfer members carrying flexible strip supports thereon and adhering the supplied strips to the flexible strip supports; changing the configuration of the flexible strip supports while the supplied strips of first material are adhered thereto, thereby correspondingly changing the configuration of the supplied strips; and moving the one or more transfer members and the web of second material into transfer contact with each other and transferring the supplied strips in their changed configuration to the web of the second material.

In one aspect of the invention, the discrete strips of first material are applied to a moving web of the second material and the method also includes the following steps: supplying one or more strips of first material to a transfer means comprising a plurality of the transfer members; moving the transfer members through a supply zone and a transfer zone, the first material being supplied to the moving transfer members in the supply zone, cutting the strips of first material to form one or more discrete strips thereof adhering to the flexible strip supports of the transfer members; and moving a web of the second material concurrently with the path of the transfer means in the transfer zone and therein transferring the discrete strips of first material from the transfer means to the moving web of second material.

In accordance with another aspect of the invention, the first material is adhered to the flexible strip supports of the transfer members in a linear configuration, and the configuration of the flexible strip supports, and thereby the configuration of the strips adhered thereto, is changed to a curvilinear configuration prior to transferring the strips to the second material. As used herein and in the claims, the term "linear configuration" as applied to the strips of first material and the flexible strip supports means that the longitudinal axis of the member so described lies substantially in a single plane, although it may be straight or curved in the plane.

Yet another aspect of the invention includes supplying the first material to the transfer means in the form of one or more continuous strips of first material and cutting the first material between the supply zone and the transfer zone to provide the discrete strips.

The invention also contemplates that the first material may comprise an elastic material and includes the steps of tensioning the (elastic) strips and applying the discrete strips under tension to the web of second material.

In accordance with the present invention there is also provided a method of applying discrete strips of a first material in a predetermined pattern to a moving web of a second material, the method comprising the following steps: supplying one or more strips of first material to a transfer means comprising a rotatable support on which a plurality of transfer members are mounted for continuous orbiting along a closed path passing through a supply zone and a transfer zone, the first material being supplied to the moving transfer members in the supply zone; cutting the one or more strips of first material to form one or more discrete strips thereof on respective ones of the transfer members; moving a web of second material concurrently with the transfer means and into transfer contact therewith in the transfer zone and therein transferring the discrete strips of first material from the transfer means to the moving web of second material and imposing a first orbital radius on transfer members in the supply zone and a second orbital radius on transfer members in the transfer zone whereby to impart a first linear velocity to transfer members in the supply zone and a second linear velocity to transfer members in the transfer zone.

Other aspects of the invention include one or more of the following, in any combination: imposing a substantially constant angular velocity on the transfer members; imposing a first orbital radius which is greater than the second orbital radius whereby the linear speed of the transfer means is greater in the supply zone than in the transfer zone; imposing a first orbital radius which is less than the second orbital radius whereby the linear speed of the transfer means is greater in the transfer zone than in the supply zone; and radially pivoting the transfer members to selectively orient the discrete strips relative to the web of second material (As used herein and in the claims, the term "radially pivoting" or the like as applied to the transfer members means pivoting the transfer member about an axis transverse to its strip carrying surface.)

Yet another aspect of the invention provides that the first material is selected from the class consisting of elastic materials and materials activatable by one or both of heat and moisture from a substantially non-elastic to an elastic state. The web of second material comprises a material utilizeable in a disposable diaper, and includes the additional steps of cutting the web of second material into individual pieces and making disposable garments, e.g., diapers therefrom.

In accordance with the present invention there is also provided apparatus for applying discrete strips of a first material in a predetermined pattern to a web of second material, the apparatus comprising: one or more transfer members carrying one or more flexible strip supports thereon; adjusting means operatively connected to the flexible strip supports to selectively change the configuration thereof; supply means for supplying one or more discrete strips of the first material to the transfer members and adhering the discrete strips to the flexible strip supports; and means to move the one or more transfer members and the web of second material into transfer contact with each other to transfer the discrete strips of first material from the strip supports to the web of second material.

In accordance with another aspect of the invention, the means to move the one or more transfer members and the web of second material into transfer contact with each other comprises transfer means comprising a rotatable support on which the transfer members are mounted for continuous orbiting along a closed path, and web transport means for moving a web of second material concurrently with a portion of the closed path.

Other aspects of the invention provide one or more of the following features, in any combination: the transfer members include at least one configured anvil surface to which the flexible strip supports are conformed by the adjusting means whereby the desired configuration is imparted to the flexible strip supports; the one or more anvil surfaces have a curvilinear configuration; a plurality of flexible strip supports are provided on respective transfer members and a plurality of anvil surfaces are respectively associated therewith; the adjusting means comprises strip support drive means which are operatively connected to the flexible strip supports to selectively move the latter between a supply position in which the flexible strip supports are configured to receive a linear strip of first material thereon, and a transfer position in which the flexible strip supports are conformed to a respective anvil surface; the transfer members include one or more stop surfaces and the flexible strip supports in the supply position are conformed to respective stop surfaces.

In accordance with another aspect of the invention, there is provided apparatus for applying discrete strips of a first material in a predetermined pattern to a web of second material, the apparatus comprising; a rotatable support on which a plurality of transfer members are mounted by translative supports for continuous orbiting of the transfer members along a closed path passing through a supply zone and a transfer zone; drive means to rotate the rotatable support; supply means disposed in the supply zone for supplying one or more discrete strips of the first material to the transfer members; web transport means disposed in the transfer zone for moving a web of second material concurrently with the closed path in the transfer zone; and radius-adjusting means operatively connected to the translative supports to selectively adjust the orbital radius of the transfer members to a first radius suitable to receive the strips of first material in the supply zone and to a second radius suitable to transfer the strips of first material to the web of second material in the transfer zone.

In accordance with another aspect of the invention, the rotatable support comprises a rotating member having radial support arms thereon, and the radius-adjusting means comprises (i) a carriage frame on which the transfer members are carried, the carriage frame being mounted for reciprocating movement on the radial support arms and carrying cam followers thereon, and (ii) a radially eccentric cam track which defines the travel path of the carriage frame and with which the cam followers on the carriage frame are engaged, whereby rotation of the rotatable member causes the carriage frame to follow the cam track thereby imposing different orbital radii on respective transfer members in different zones of the cam track.

Other aspects of the invention provide one or more of the following features in any combination: the cam track is displaced radially outwardly in the supply zone relative to its radial track in the transfer zone; the cam track is displaced radially outwardly in the transfer zone relative to its radial track in the supply zone; the apparatus further includes means for radially pivoting the transfer members to selectively orient the flexible strip supports relative to a web of second material carried on the web transport means.

A BRIEF DESCRIPTION OF THE DRAWINGS

FIG. 1 is a perspective view of a finished disposable diaper comprising one style end product attainable by utilizing the method and apparatus of the present invention;

FIG. 2 is a perspective view of a segment of material in an intermediate stage of manufacture of the diaper of FIG. 1;

FIG. 3A is a plan view of a segment of a web of second material having thereon curvilinear strips of a first material, in an intermediate stage of manufacture of another style of a disposable diaper;

FIG. 3B is a schematic view in side elevation of an apparatus for applying the curvilinear strips of first material to the web of second material as illustrated in FIG. 3A;

FIG. 3C is a schematic perspective view showing one of the elements of the apparatus of FIG. 3B in three different stages of operation;

Figure 8:
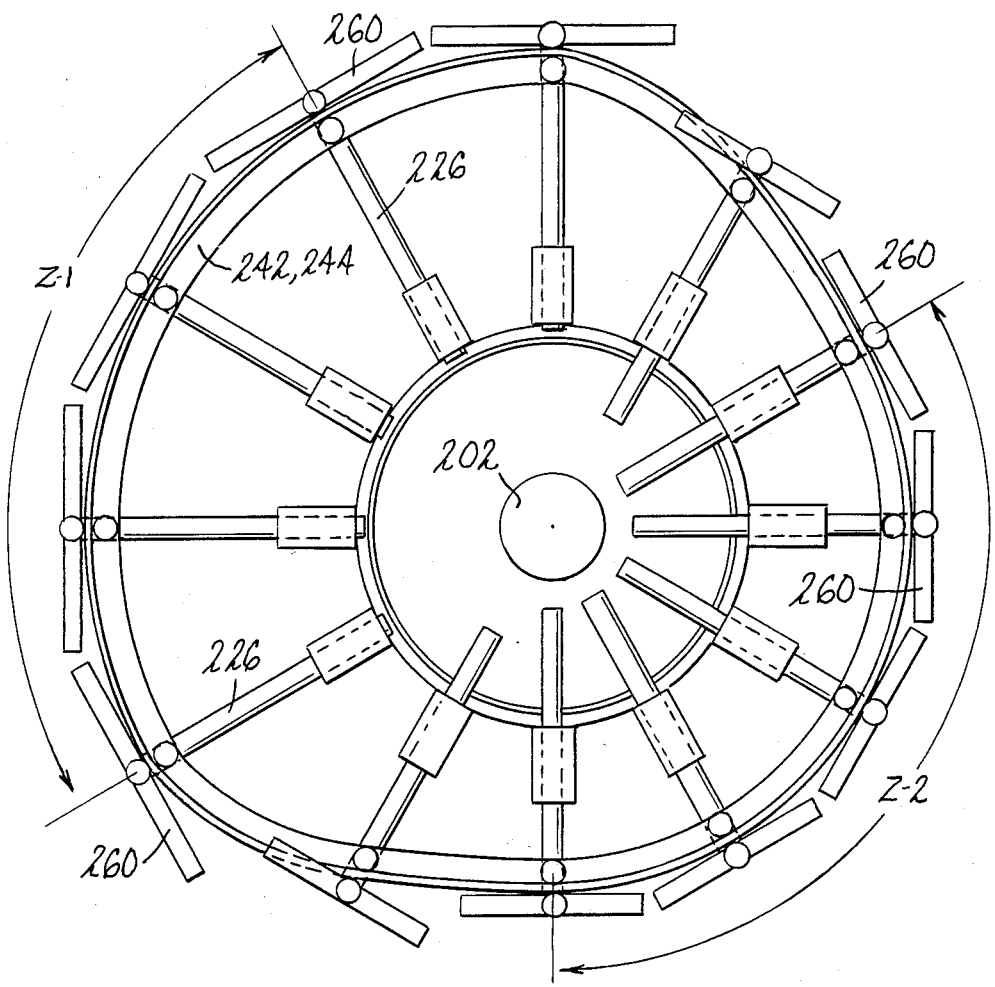
Figure 7A:
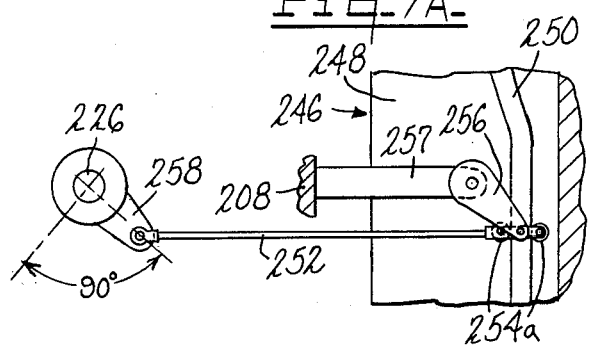

FIGS. 4A, 4B and 4C correspond, respectively, to FIGS. 3A, 3B and 3C but illustrate another mode of utilizing the apparatus to provide a differently configured product;

FIGS. 5A, 5B and 5C correspond, respectively, to FIGS. 3A, 3B and 3C but illustrate yet another mode of utilizing the apparatus to provide a differently configured product;

FIG. 6 is an end view in elevation of one embodiment of the transfer means of the present invention in which the transfer members have a uniform orbital radius and are radially pivotable about their supports during each rotation cycle;

FIG. 7 is a view on an enlarged scale generally corresponding to the upper half of FIG. 6 but showing another embodiment of the transfer means of the invention in which the transfer members are mounted for adjustment of their respective orbital radii during each rotation cycle in addition to being radially pivoting to adjust their orientation;

FIG. 7A is a partial view taken along line 7A—7A of FIG. 7;

FIG. 8 is a schematic side view in elevation showing the orbital travel paths of elements of an apparatus of the type illustrated in FIG. 7;

FIG. 9 is a plan view of one embodiment of a transfer member utilizable in the apparatus of FIG. 7;

FIG. 10 is a side view in elevation of the transfer member of FIG. 9;

FIG. 11 is an end view in elevation of the transfer member of FIG. 9; and

FIG. 12 is a bottom plan view of the transfer member of FIG. 9.

DESCRIPTION OF THE PREFERRED EMBODIMENTS

FIG. 1 illustrates a typical finished disposable diaper comprised of a top sheet 2 and a back sheet 4 between which is sandwiched a liquid absorbent pad or sheet which is not shown although its bulk is indicated by the thickness of the finished article, particularly in the crotch area 6 disposed intermediate rear waist area 8 and front waist area 10. As well known in the art, top sheet 2 is formed of a liquid pervious material and backsheet 4 is formed of a liquid impervious material such as a suitable synthetic organic polymeric material, e.g., a polyolefin plastic film. Leg areas 12, 14 are cut out and a portion thereof is bordered by elastic strips 16, 18 which are fastened between top sheet 2 and back sheet 4 and affixed to the latter by a suitable adhesive or by other means such as ultrasonic welding. Waist fastening tapes 20, 22 are affixed to the diaper in the usual manner. When fitted about the wearer, waist fastening tapes 20, 22 are secured over back sheet 4 in front waist area 10 to hold the diaper in place. Prior to the diaper being applied to the wearer, elastic strips 16, 18 are in a relaxed condition as illustrated in FIG. 1 in which they cause random pleating of the top sheet and back sheet as shown in the drawing. Upon the diaper being applied to the wearer, elastic strips 16, 18 serve to elasticize leg areas 12, 14 to provide a snug fit about the legs of the wearer.

FIG. 2 shows a segment of a continuous web 24 which eventually will be cut transversely at the locations indicated by the dashed lines r to provide a plurality of back sheets 4. Web 24 will also be cut as indicated by the dotted lines 12', 14' to form the leg areas 12, 14. A plurality of discrete elastic strips 16, 18 are applied in linear and spaced apart configuration along continuous web 24 and secured thereto by a suitable adhesive.

FIG. 3A shows in plan view a continuous web 24 similar or identical to that illustrated in FIG. 2, but on which a plurality of spaced apart elastic strips 16a, 18a have curvilinear configurations which, as illustrated, include sharp curves. The severe change in direction of the elastic strips in such a short linear distance travel of the web 24a (indicated by the arrow in FIG. 3A) could not be attained by simply oscillating an elastic strip feed head over the moving web because of the extraordinarily high velocities that would be required to accommodate the velocity of web 24a, which may be 600 feet per minute or more.

This problem is overcome in accordance with the aspect of the invention schematically illustrated in FIG. 3C, which shows an elastic strip supply roller 28 which is feeding two continuous strips 16', 18' of elastic material onto transfer members comprising a platen 30 on which are mounted a pair of flexible strip supports 32. As described in more detail below, flexible strip supports 32 may be selectively manipulated to change their configuration from, for example, the linear configuration shown at station A of FIG. 3C to the curvilinear configuration shown at station C of FIG. 3C. Stations A, B, and C of FIG. 3C show, respectively, sequential stages in the operation which are also indicated at, respectively, stations A, B, and C of FIG. 3B. FIG. 3B shows a schematic version of apparatus in accordance with one embodiment of the invention, in which a plurality of transfer means 30 are mounted on a rotatable support means generally indicated at 34 and comprising a cylindrical or wheel-like carriage means 36 mounted for rotation upon a rotatable shaft 38 by a plurality of spoke members 40 emanating from a hub portion (unnumbered) mounted to rotate with shaft 38. Spoke members 40 support an annular shaped web portion 41 which supports carriage portion 42 which provides a wide, drum-like structure, axially opposite ends of which may be received within a plurality of guide rollers 44. The opposite ends of shaft 38 and the guide rollers 44 are mounted on a pair of opposed vertical wall stanchions 46, 46a, the latter being broken away for clarity of illustration. Guide rollers 44 are mounted on the broken-away portion of wall stanchion 46a and corresponding guide rollers, not visible in FIG. 3B, are mounted on wall stanchion 46, to supportingly engage the opposite periphery of carriage portion 42. Each transfer member 30 is mounted upon a respective support 48 carried by carriage portion 42 and a respective bearing member 50 affixed to web portion 41 of carriage means 36.

In the embodiment shown, rotatable support means 34 rotates in the direction indicated by the circular arrow D whereby transfer members 30 are carried in a closed, orbital path passing through a supply zone S and a transfer zone T in each rotation cycle.

As mentioned above, elastic strip supply roller 28 feeds a pair of elastic strips 16', 18' to a transfer member 30 in the supply zone S comprising the indicated portion of the orbital path defined by transfer members 30 as rotatable support means 34 rotates in the direction indicated. A pressure roller 52 (shown in FIG. 3B but not in FIG. 3C) presses the elastic strips 16', 18' to adhere them to flexible strip supports 32 and a rotating cutter means 54 cuts the continuous strips 16', 18' to discrete strips 16, 18 adhered to respective flexible strip supports 32. The discrete strips 16, 18 may be adhered to flexible strips supports 32 by any suitable means. One preferred method is to utilize as the elastic strip material a self-adhering elastic material such as that sold under the trademark FULLASTIC by H. B. Fuller Company, Louisville, Ky, U.S.A. Such material is described in U.S. Pat. Nos. 4,259,220 and 4,418,123, the disclosures of which are incorporated by reference herein. In such case, the flexible strip supports 32 are made of a compatible material to which the self-adhering elastic strip material will adhere sufficiently for purposes of the invention and from which the elastic strips can be removed for transfer to web of material as described below. Obviously, other suitable methods may be employed to temporarily adhere the elastic strips to the flexible strip supports. For example, vacuum may be supplied to openings on the top surface of flexible strip supports 32 to hold the elastic strips in place, or mechanical clamping means may be utilized. In any event, pressure roller 52 serves to firmly but temporarily adhere elastic strips 16', 18' to flexible strip supports 32. As indicated at station A (FIGS. 3B and 3C) the leading end of strips 16', 18' has been cut by cutter 54 and as the leftward (as viewed in FIG. 3C) end of flexible strip supports 32 passes beneath cutter 54 the trailing end of the strips will be likewise cut to provide the discrete strips 16, 18. As transfer member 30 leaves station A, moving clockwise as viewed in FIG. 3B and rightwardly as viewed in FIG. 3C, the configuration of flexible strip supports 32 is changed by configuration-changing means (not shown in FIG. 3B and described in detail below) from a linear configuration as shown at station A of FIG. 3C to an intermediate curvilinear configuration as shown at station B of FIG. 3C (the location of station B is shown in FIG. 3B). During its travel after leaving cutter 54 and prior to its arrival at station C, flexible strip support means 32 is changed to its final curvilinear configuration shown at station C of FIG. 3C (the location of station C is shown in FIG. 3C). The travel time after leaving cutter 54 and prior to arriving at station C is sufficient to impart any desired configuration to flexible strip supports 32 and thereby to the discrete elastic strips 16, 18 adhered thereto. At station C, transfer member 30 is about to enter transfer zone T in which the discrete elastic strips 16, 18 are transferred to a continuous web 24a of second material which is transported by means of transport rollers 56a, 56b and 56c and transfer roller 58 in the direction indicated by the arrow associated with web 24a in FIG. 3B. The adhesion strength of discrete strip 16, 18 on flexible strip supports 32 is considerably less than the adhesive attraction between discrete strip 16, 18 and web 24a so that the discrete strips are removed from flexible strip supports 32 and transferred to web of second material 24a in the transfer zone T. Obviously, an adhesive may be employed to secure strips 16, 18 to a web 24a and this adhesive may be applied to the strips 16, 18 while they are supported on the flexible strip supports 32, or adhesive may be applied to web 24a in a desired pattern, or both. Any other means, e.g., ultrasonic welding, may be employed to securely attach the strips to a web 24a.

With reference to FIG. 3B, it should be noted that the diameter of transfer roller 58 is sized so that continuous web 24a is separated from transfer member 30 at an angle (angle a in FIG. 3A) large enough to insure removal of the discrete strips 16, 18 from strip supports 32. Angle a is the angle formed between the support surface of strip supports 32 and a tangent to the outer diameter of transfer roller 58 at the point where it presses web 24a into contact with strip supports 32 of transfer members 30. This angle must be large enough so that the adhesive force between the flexible strip supports and the discrete strips of first material is overcome by the adhesive force between web 24a and the discrete strips.

After leaving transfer zone T the configuration of flexible strip supports 32 is returned by the configuration-changing means (not shown in FIG. 3B) to a straight or linear configuration so that upon entering supply zone S continuous elastic strips 16', 18' may be fed thereto to repeat the cycle. The resultant product is shown in plan view in FIG. 3A comprising the continuous web 24a of second material having thereon a plurality of curvilinear elastic strips 16a, 18a which have a sharp curvature as indicated in FIG. 3A. It will be appreciated that the method and means described to impart the curvilinear configuration to strips 16a, 16b are not limited by the linear speed of movement of web 24a.

Generally, supply roller 28 and pressure roller 52 together with cutter 54 comprise one embodiment of supply means for supplying one or more discrete strips of first material to the transfer means. Similarly, transport rollers 56a, 56b and 56c, together with transfer roller 58 comprise one embodiment of web transport means.

For the making of disposable diapers, absorbent material and a top sheet may be applied to web 24a, and the resulting composite cut transversely at the places indicated by the dashed lines r in FIG. 3A to provide individual disposable diapers or other garments in which the curvilinear elastic strips 16a, 18a are utilized as the leg elastics to provide a snug, contour fitted leg opening in the garment.

FIGS. 4A, 4B and 4C generally correspond to, respectively, FIGS. 3A, 3B and 3C. Parts in FIG. 4B (and in FIG. 5B) which correspond to parts in FIG. 3B are identically numbered and other parts in FIGS. 4B and 5B have been omitted or broken away for improved clarity of illustration. FIGS. 4A, 4B and 4C illustrate an embodiment of the invention wherein supports 48 of transfer members 30 are radially translatable, i.e., are movable radially inwardly and outwardly in their respective bearing members 50, so that the effective orbital radius of individual transfer members 30 may be selectively adjusted to different radii at different zones of a single rotation cycle. In this way, selected different linear speeds are imposed on transfer members 30 in different zones of the closed orbital path through which the transfer members 30 travel. This feature of selectively imposing different orbital radii and thereby different linear velocities on the transfer members 30 in different zones of the closed path is particularly advantageous in that it permits the utilization of independent linear supply speeds of the web 24a and elastic strips 16', 18. This permits a greater or lesser length of elastic strip to be applied to each repeat length to be cut from web 24a. Generally, the structure of FIG. 4B is identical to that of FIG. 3B, the transfer members 30 rotating on rotatable support means 34 in a clockwise direction through a closed path and passing through a supply zone S and a transfer zone T. In fact, the identical apparatus used in FIG. 3B may be employed in FIG. 4B provided that the construction is such that supports 48 are radially movable relative to carriage portion 42. For this purpose, supports 48 may comprise splined shafts mounted in bearing members 50 and, optionally, additional collar bearings (not shown in FIG. 4B) may be provided in carriage portion 42 to further support the splined shafts comprising support 48. An additional feature of the apparatus shown in FIG. 4B comprises a closed cam path 60 which may be mounted on wall stanchion 46 (not shown in FIG. 4B) and within which are received rollers comprising cam followers 62 fitted to the radially inner ends of supports 48. Cam 60 may comprise a track on one or both of wall stanchions 46, 46a (not shown in FIG. 4B) or may be provided on a cylindrical, barrel-like structure (of the type illustrated in FIGS. 6 and 7) which is mounted on one or the other of the wall stanchions. As seen in FIG. 4B, cam 60 defines an eccentric path relative to the center of rotation defined by the rotational axis of rotatable shaft 38 so that the orbital radius of a transfer member 30 in supply zone S is less than the orbital radius of a transfer member 30 in transfer zone T. Since the angular velocity of each transfer member 30 is constant, the linear velocity of the transfer members 30 in transfer zone T is greater than the linear velocity of transfer members in supply zone S. In orbiting between supply zones S and T the linear velocity of the transfer members increases as the orbital radius thereof increases by virtue of cam followers 62 following cam track 60 and thereby sliding translatable supports 48 radially outwardly relative to the axis of rotation of rotatable shaft 38. In this manner, web 24a may be operated at a linear speed greater than the linear speed at which continuous elastic strips 16', 18' are supplied in the supply zone S.

It will be apparent that by selecting a desired configuration of the closed path defined by cam 60, the orbital radius and consequently the linear velocity of transfer members in the supply zone may be made greater (or lesser) than those in the transfer zone and a selected orbital radius and concomitant linear velocity may be selected along any segment of the closed orbital path of the transfer members 30. This flexibility can provide very significant advantages. For example, the length of an individual discrete strip 16a or 18a may be made greater or less than the length of the repeat (the distance in the direction of web travel between dashed lines r) of the web 24a of second material.

The apparatus illustrated in FIG. 5B is similar or may be identical to that shown in FIGS. 3B and 4B, but is capable not only of changing the configuration of the flexible strip supports and the orbital radius of the transfer members but also of selectively radially pivoting supports 48 about their longitudinal axes. This pivoting changes the orientation of transfer members 30, and thereby of flexible strip supports 32, between the supply zone S and the transfer zone T. In FIG. 5B, cam 60 is seen to provide a larger orbital radius and therefore a higher linear velocity to transfer members in supply zone S than in transfer zone T. This permits the application to each transfer member 30 of a length of elastic strip 16', 18' longer than the repeat of web 24a. In this embodiment, means are also provided to enable radially pivoting supports 48 (and transfer member 30) about their respective longitudinal axes a selected amount, e.g., 90 degrees, to change the orientation of the discrete strips 16, 18 of first material relative to web 24a. Generally, the apparatus of FIG. 5B includes a cam track 60 and cam followers 62, and has supports 48 mounted in bearings 50 for radial translation relative to rotatable shaft 38 and pivoting movement about their own longitudinal axes.

In operation, as transfer members 30 pass through supply zone S, cam followers 62 following cam 60 thrust supports 48 radially outwardly thereby imposing upon them an orbital velocity greater than their orbital velocity in transfer zone T and moving them concurrently with elastic strips 16', 18' supplied by supply roller 28 and pressed into adhering contact with flexible strip supports 32 by pressure roller 52. After leaving supply zone S cutter 54 cuts elastic strips 16', 18' into discrete strip 16a, 18a. After leaving the area of cutter 54 a pivoting motion about their longitudinal axis is imposed upon supports 48 by means not shown in FIG. 5B but equivalent to those described in detail with respect to FIGS. 6 and 7. Transfer members 30 are correspondingly pivoted as indicated by the rotational arrows and axis lines shown in FIG. 5B in the vicinity of station C. Upon arrival at station D, a 90° orientation change of transfer members 30 has been effectuated. In addition, the configuration of flexible strips supports has been changed from the linear configuration shown at station B of FIG. 5C to the full curvilinear configuration shown at station D. The curvilinear configured strips 16a, 18a are therefore applied to web 24a at transfer zone T in the 90 degree rotated orientation (relative to their orientation in supply zone S) and in the curvilinear configuration shown at station D of FIG. 5C and in FIG. 5A.

It will be appreciated that any one or more of the three features of (a) changing the configuration of the flexible strip supports and thereby of the discrete elastic strips adhered thereto, (b) changing the orbital radius of the transfer members in the different zones of the closed orbital path through which the transfer members move and (c) changing the orientation of transfer members 30 between the supply zone S and the transfer zone T, may be employed individually or in any combination. The advantages thus provided by the invention will be apparent to those skilled in the art upon a reading and understanding of the foregoing. It is seen that the elastic strips may be supplied at a linear speed independent of the linear speed of the web of material to which the strips are to be applied, so that a length of elastic strips greater than, equal to or less than the repeat length of the web may be utilized, and configurations including sharply curvilinear configurations may be imposed on the elastic strips independently of the web travel speed.

Referring now to FIG. 6, there is shown an end elevation view of one embodiment of the transfer means of the invention generally indicated at 100, neither the supply means to supply elastic strips nor the web transport means to supply the web of second material being shown in FIG. 6. Only two of a larger number of transfer members 146 and their supports 114 are shown in FIG. 6, for enhanced clarity of illustration. Transfer means 100 comprises a rotatable shaft 102 mounted for rotation in a pair of opposed wall stanchions 104, 106 and on which a rotatable support means generally indicated at 108 is mounted for rotation with shaft 102. Rotatable support means 108 comprises a spider hub portion 110 having a plurality of shaft bearings 112 mounted thereon to receive supports (shafts) 114 of transfer members 116. Carriage means 118 comprises, in this embodiment, a cylindrical carriage frame 120 having annular peripheral edge collars 122, 124 extending along opposite edges thereof and reinforced at intervals by flanges 126. A plurality of roller cam followers 128 are mounted at spaced apart locations along, respectively, annular peripheral collars 122 and 124 and are engaged within a track provided by cam tracks 130, 132 mounted on respective facing walls of wall stanchions 104, 106. In the embodiment illustrated, cam tracks 130, 132 are circular in plan view, the device illustrated in FIG. 6 being one designed to operate with a constant orbital radius of the transfer members 116. In embodiments wherein it may be desired to substitute non-circular, i.e., eccentric, versions of cam tracks 130, 132, individual carriage frames for each transfer member 116 are provided, as in the FIG. 7 embodiment.

A barrel cam 134 is mounted on the interior facing wall of wall stanchion 104 concentrically with cam tracks 130, 132 and has a spiral cam track 136 extending annularly around the periphery of barrel cam 134. Connecting shafts 138 are connected eccentrically to pivot links 140 which are in turn connected to supports 114 so that pivoting of pivot links 140 will pivot supports 114 about their respective longitudinal axes. The opposite ends of connecting shafts 138 are connected to roller cam followers 142 which engage spiral cam track 136 of barrel cam 134. A plurality of collar bearings 144 receive respective support shafts 114 pivotably within cylindrical carriage frame 120.

In operation, rotation of shaft 102 by a schematically shown drive means 98 carries rotatable support means 108 and with it, thereby rotating cylindrical carriage frame 120 therewith, the latter being guided by cam tracks 130, 132 for rotation concentrically with shaft 102. As cam followers 142 follow spiral cam track 136, transfer member 116 is pivoted by pivoting supports 114 through 90° between its position shown at the bottom of FIG. 6 and its position shown at the top of FIG. 6. (Operation of a similar spiral cam/pivot link arrangement is described in more detail with respect to FIG. 7A). With shaft 102 rotating in the direction indicated by the curved arrow at the left end (as viewed in the drawing) of shaft 102 the leading edge 116a of transfer member 116 at the bottom of the drawing is visible head-on, as are the leading ends of strip supports 146. The cam follower 142 at the bottom of FIG. 6 is retained by spiral cam track 136 at its leftward most position as viewed in the drawings, pivot link 140 being positioned at that point to orient strip supports 146 such that they are longitudinally aligned with the orbital path of rotation of transfer member 116. As rotation continues, spiral cam track 136 forces roller cam followers 142 rightwardly as viewed in the drawings so that by the time a transfer member 146 reaches the position at the top of FIG. 6, cam follower 142 is in its rightward most position and pivot link 140 associated therewith has been moved rightwardly to complete a 90° pivoting of support 114 about its own longitudinal axis in its bearing 112. At this juncture the side edge 116b of transfer member 116 (at the top of the drawing) is visible head-on as is the side edge of one of support strips 146, which are now oriented transversely to the direction of orbiting of transfer member 116.

It will be appreciated by those skilled in the art that the structure shown in FIG. 6 is somewhat simplified and that numerous parts (e.g., to insure retention of cam followers on the cam track, etc.) have been omitted for clarity of illustration. It will further be apparent that by appropriate design of spiral cam track 136 and its associated linkage to supports 114, any desired degree of pivoting of transfer members 116 may be effectuated. In the embodiment illustrated, the supply zone in which the continuous thin strip material is supplied to strip supports 146 would be located at or near the bottom of FIG. 6 and the transfer zone in which the strips are transferred in their transversed position to the web of second material would be at or near the top of FIG. 6. A change in orientation greater or lesser than 90° may obviously be utilized, as desired.

Referring now to FIG. 7, there is shown another embodiment of the invention which provides not only for pivoting of the transfer members about their supports to selectively change orientation of the transfer members, but for selectively changing the orbital radius of the transfer members and the configuration of the flexible strip supports.

FIG. 7 shows only a portion of the transfer means and omits the supply means and web transport means which would be associated therewith. Only one of a plurality of transfer members and associated carriage frames is shown. The transfer means of the embodiment of FIG. 7 is generally indicated at 200 and comprises a rotatable shaft 202 mounted, like the embodiment of FIG. 6, between a pair of opposed wall stanchions which, however, are not shown in FIG. 7. Rotatable support means indicated generally at 204 comprise in the illustrated embodiment a plurality of radial support arms 206, 208, secured by means of arm mounting members 210, 212 which are affixed to rotatable shaft 202 for rotation therewith. As seen in FIG. 7, radial support arms 206, 208 are provided in pairs which are longitudinally aligned on shaft 202 and each radial arm has a respective radially extending track 214, 216 thereon, tracks 214 and 216 being parallel to each other and lying in the same plane passing through the longitudinal axis of rotation of shaft 202. A bearing support element 218 has shaft bearings 220, 222 mounted thereon and is itself mounted for rotation with shaft 202 by bearing mounting means 224. In this embodiment, support 226 comprises a splined shaft rotatably mounted within shaft bearings 220, 222 and extending through a roller bearing collar 228 which is mounted on carriage frame 230. Each carriage frame 230 is mounted by means of its associated carriage trolleys 232, 234 which are respectively mounted on radially extending tracks 214, 216 for sliding movement thereon. End plates 236, 238 are formed respectively at the opposite side ends of carriage frame 230 and carry respective sets of roller cam followers 240 mounted thereon. Reinforcing flanges (not shown in FIG. 7) may be used to help secure annular peripheral collars 238, 234 through carriage frame 230 in the same manner as indicated in the embodiment of FIG. 6. Each transfer member is mounted in the manner described on its associated carriage means and shaft bearings.

Cam tracks 242, 244 are mounted on the facing interior wall of the wall stanchions (not shown) and roller cam followers 240 are engaged therewith so that upon rotation of transfer means 204 the cam followers and consequently each carriage frame 230 is compelled to follow the track of cam tracks 242, 244. In the embodiment illustrated, as will be described with respect to schematic FIG. 8, cam tracks 242 and 244 are closed tracks eccentric in plan view and the mirror image of each other.

Mounted on the interior of the same wall stanchion (not shown) on which cam track 244 is mounted, is barrel cam 246 comprising a cylindrical barrel 248 having a spiral cam track 250 extending about the exterior periphery thereof in a manner similar to that illustrated in the FIG. 6 embodiment. A connecting shaft 252 (FIGS. 7 and 7A) is connected at the tracking end thereof to a roller cam follower assembly 254 comprising, as best seen in FIG. 7, a pair of rollers 254a engaging respectively opposite sides of spiral cam track 250. A connector link 256 has one end mounted on cam follower assembly 254 and is pivotably connected to the tracking end of connecting shaft 252. The other end of connector link 256 is pivotably mounted on pivot link support arm 257 which is secured by supporting flange 259 to radial support arm 208. The distal or free end of connecting shaft 252 is connected to pivot collar 258 which is non-rotatably mounted on support 226 in the splined shaft portion thereof. Support 226 is, however, slideable longitudinally in pivot collar 258. Transfer member 260 is affixed non-rotatably to the radially outward end of support 226 by locking collar 226.

In operation, as shaft 202 rotates radial support arms 206, 208 and bearing support element 218 are constrained to rotate therewith. Carriage frame 230, being mounted upon radial support arms 206, 208 by means of carriage trolleys 232, 234 likewise is constrained to rotate with the rotation of shaft 202. Roller cam followers 240 follow the track provided by cam tracks. In cases where cam tracks are circular and concentrically disposed with respect to the longitudinal axis of rotation of shaft 202, carriage trolleys 234, 236 remain a fixed radial distance from the longitudinal axis of shaft 202. However, if cam tracks 242, 244 (as in the illustrated embodiment) are eccentrically configured with respect to the longitudinal axis of rotation of shaft 202, carriage frame 230 is constrained to follow the eccentric path thereby moving transfer member 260 in radial translation motion relative to rotating shaft 202, and correspondingly increasing and decreasing the effective orbital radius of the transfer members. This may be appreciated by reference to FIG. 8 which shows a schematic side elevation view indicating the travel path of components of the transfer means of an apparatus of the type illustrated in FIG. 7. Parts corresponding to those of the FIG. 7 embodiment are correspondingly numbered. Thus, a plurality of transfer members 260 are shown mounted upon respective support shafts 226 carried on bearings 220. Rotatable shaft 202 is shown in its relative position to the transfer members and the track of cam tracks 242, 244 is indicated. For clarity of illustration, parts such as those corresponding to carriage frame 230, shaft bearings 222, radial support arms 206, 208, etc. are omitted from the schematic diagram of FIG. 8. As carriage frame 230 rotates along the course on which it is constrained by cam tracks 242, 244 it describes eccentric rotation relative to shaft 202, which eccentric motion is accommodated by the radially translating travel of carriage trolleys 232, 234 along tracks 214, 216 of respective radial arms 206, 208 (FIG. 7). Thus, as viewed in FIG. 8, transfer members 260 when traveling through zone Z-1 of their closed orbital path are at their radially outermost position and while traveling through zone Z-2 are at their radially innermost position. Since the angular speed of rotation is determined by the speed of rotation of rotatable shaft 202, individual transfer members 260 have a uniform angular speed and their linear speed along their orbital path varies directly with their effective orbital radius, i.e., the radius distance between transfer members 260 and the longitudinal axis of rotation of shaft 202.

In addition to the change in orbital radius, spiral cam 250 (FIGS. 7 and 7A) will act on connecting shaft 252 to provide a desired degree of pivoting of transfer members 260 as they travel along their closed orbital path of travel to change the orientation thereof. This occurs by roller cam follower assembly 254 following spiral cam track 250 and pivoting pivot collar 258 90° to the position shown in dotted lines in FIG. 7A. Pivoting of the transfer members may be selected to change their orientation, and that of the strips of first material carried thereon, any desired amount.

Referring now to FIGS. 9–12, FIG. 9 shows a plan view of a transfer member 260 which, as best seen in FIGS. 10 and 11, has a generally beveled upper surface 264 on which are formed a pair of raised lands 266, 266a having respective curvilinear anvil surfaces 270, 270a. As best noted in FIGS. 9 and 11, anvil surfaces 270, 270a are slightly undershot, that is, the anvil surfaces 270, 270a are disposed at a slight angle to the vertical with the upper portion thereof projecting in a slight overhang.

A pair of flexible strip supports 272, 274 are mounted on upper surface 264 and are shown in FIG. 9 in their linear configuration. Thus, when the flexible strip supports are in their "linear configuration" their longitudinal axes lie in a single plane so that they give a straight line projection in the plan view of FIG. 9, but are gently curved in the side elevation view of FIG. 10. As best seen in FIG. 11, flexible strip supports 272, 274 are generally trapezoidal shaped in cross section so as to matingly engage the slightly undershot respective anvil surfaces 270, 270a. A central raised land portion 278 is substantially rectangular in projected configuration as seen in FIG. 9 and provides a pair of opposed stop surfaces 280, 282.

Adjacent opposite ends of flexible strip supports 272, 274, curvilinear slots 284a, 284b and 286a, 286b are formed along the outer periphery of upper surfaces 264.

Through respective ones of these slots mounting pins 288 (FIGS. 10 and 11) are secured to pivot arms 290a, 290b, 290c and 290d, as best seen in FIG. 12. Mounting pins 288 have enlarged heads at one end which are embedded within respective opposite ends of flexible strip supports 272, 274. Locking nuts 292 secure mounting pins 288 to respective ones of pivot arms 290a–d. The central body portion of mounting pins 288 extend through respective ones of slots 284a, 284b, 286a and 286b. In this manner, upon travel of mounting pins 288 through their associated slots as described in more detail below, flexible strip supports 272, 274 are moved from their linear configuration aligned with and held against stop surfaces 280, 282 respectively to a curvilinear configuration conforming to respective ones of anvil surfaces 270, 270a. The latter curvilinear configuration is shown in dot-dash outline in FIG. 9. Flexible strip supports 272, 274 may be made of any suitable material such as a synthetic organic polymeric material having flexible or elastomeric properties. At least the top surface of supports 272, 274 are preferably made of a material to which self-adhering elastic strips will adhere with sufficient strength so that upon changing the configuration of the flexible support 272, 274 from the linear configuration shown in solid line in FIG. 9 to the curvilinear configuration shown in dot-dash outline in FIG. 9, the discrete elastic or other strips adhered thereto will have their configuration similarly changed.

Referring now particularly to FIGS. 10–12, the under surface 294 of transfer member 260 is seen in FIG. 12 and has secured thereto a mounting collar generally indicated at 296 which is secured to transfer member 260 by a bolt-like fastening means (not shown) inserted through stepped mounting opening 298 as best seen in FIGS. 9 and 11. Mounting collar 296 is configured and dimensioned to be received over the upper (as viewed in FIG. 7) end of support shaft 226 and to engage roller bearing collar 228 mounted on carriage frame 230. As schematically indicated in FIG. 12, a drive gear 300 is non-rotatably affixed to mounting collar 296 so that upon pivoting of support shaft 226 drive gear 300 drives secondary gears 302, 304 which in turn drive spur gears 306, 308, 310 and 312. With the arrangement shown, upon pivoting of support shaft 226 to change the orientation of transfer members 260 as described above, pivot arms 290a, 290b, 290c and 290d are respectively pivoted in the direction of the arrows associated therewith in FIG. 12, with the result that flexible strips 272, 274 are moved into conformity with respectively, anvil surfaces 270 and 270a thereby changing their configuration from a linear configuration to a sharply curved curvilinear configuration. In this manner, the pivoting of support shaft 226 is coordinated with the changing of the configuration of flexible support strips 272, 274 so that the desired degree of transfer member pivoting, 90° in this case, is attained together with the full conformance of flexible support strips 272, 274 with anvil surfaces 270, 270a.

Generally, the strips of first material comprise strips of an elastic material and may be of any suitable configuration such as ribbons or cord-like strands. However, such strips of first material may also comprise materials which are activatable from a substantially non-elastic to an elastic state at least sufficient, for example, to adequately close and seal the leg openings of a disposable diaper or other incontinence control garment. Such activatable elastic materials include those which are activated by heat so that the strips of first material are applied in an untensioned, substantially non-elastic state to the web of second material and thereafter heated to elasticize the material. Such heat activated materials are known, (e.g., U.S. Pat. No. 3,245,407) and are commercially available for example, from 3M Company and under the trademark PEB-EX from Rilsan Corporation of Birdsborough, Pa. Alternatively, and particularly when used to make garments such as disposable diapers or other incontinence control garments, the strip of first material may comprise a moisture activatable material, that is, a material which is converted from a substantially non-elastic to an elastic condition by contact with moisture, such as urine.

Flexible strip supports 272, 274 are preferably made of a material to which a self-adhering elastic strip material (of the type discussed above with respect to U.S. Pat. Nos. 4,259,220 and 4,418,123) readily adheres. For example, flexible strip supports 272 and 274 may be made of a silicone rubber such as that supplied by American Roller Company of Union Grove, Wis. under product number 12-952.15-1531. For greater adherence or holding power, which may be required if elastic strips in the form of cord or string rather than a flat ribbon is utilized, a material such as an EPDM "artificial natural rubber" may be utilized for flexible strip supports. As shown in FIGS. 9–11, in a preferred construction flexible strip support 272 has embedded in the top surface thereof a pair of longitudinally spaced-apart transverse interrupter strips 314a, 314b. The interrupter strips are made of a material, such as brass or a urethane rubber, to which the self-adhering elastic strip will adhere with significant strength. Transverse interrupter strips 314a, 314b are respectively positioned inwardly from opposite ends 272a and 272b of strip support 272 sufficiently to provide a cutting area between each interrupter strip and its respective adjacent end. It is in this cutting area that strip is cut into discrete pieces as by the cutter 54 illustrated in FIGS. 3A–5A. Flexible strip support 274 is identically provided with transverse interrupter strips 316a, 316b. In operation, as the tensioned elastic strip is cut, it tends to snap back and release from flexible strip supports 272, 274. The interrupter strips 314a, b and 316a, b interrupt the release action, thereby helping to insure that the portion of the self-adherent elastic strip contacting the flexible strip support between the respective pairs of interrupter strips remains adhered to the flexible strip support until transferred.

It will be apparent to those skilled in the art that numerous other embodiments in accordance with the invention could be employed. For example, it might be desired to change the configuration of flexible strip supports 272, 274 without changing the orientation of transfer members 260. In such case, a collar link similar in configuration to pivot collar 258 (which, in the illustrated embodiment, serves to pivot shaft 226) would be mounted for pivoting movement with respect to shaft 226 and engaged with drive gear 300 or its equivalent to operate the gearing system which drives mounting pins 288 without pivoting shaft 226. In yet another another embodiment, two connecting shafts could be utilized for each support shaft instead of the single connecting shaft 252, and a second spiral cam track employed to control the shaft which operates the flexible strip support gearing system independently of the shaft which controls the pivoting action.

While the invention has been described in detail with respect to specific preferred embodiments thereof, it will be apparent to those skilled in the art upon a reading and understanding of the foregoing that numerous alterations and modifications may be made thereto. It is intended to include all such alterations and modifications within the scope of the following claims.

What is claimed is:

1. A method of applying discrete strips of a first material in a predetermined pattern to a web of a second material comprises:

supplying one or more discrete strips of the first material to one or more transfer members carrying flexible strip supports thereon and adhering the supplied strips to the flexible strip supports;

cutting the strips of first material to form one or more discrete strips thereof adhering to the flexible strip supports of the transfer members;

changing the configuration of the flexible strip supports while the supplied strips of first material are adhered thereto, thereby correspondingly changing the configuration of the supplied strips; and moving the one or more transfer members and the web of second material into transfer contact with each other and transferring the supplied strips in their changed configuration to the web of the second material.

2. The method of claim 1 wherein the discrete strips of first material are applied to a moving web of the second material and including the steps of:

supplying one or more strips of first material to a transfer means comprising a plurality of the transfer members;

moving the transfer members through a supply zone and a transfer zone, the first material being supplied to the moving transfer members in the supply zone; and moving a web of the second material concurrently with the path of the transfer means in the transfer zone and therein transferring the discrete strips of first material from the transfer means to the moving web of second material.

3. The method of claim 2 wherein the first material is adhered to the flexible strip supports of the transfer members in a linear configuration, and changing the configuration of the flexible strip supports, and thereby the configuration of the strips adhered thereto, to a curvilinear configuration prior to transferring the strips to the second material.

4. The method of claim 3 including supplying the first material to the transfer means in the form of one or more continuous strips of first material and cutting the first material between the supply zone and the transfer zone to provide the discrete strips.

5. The method of claim 4 wherein the first material comprises an elastic material and including the steps of tensioning the strips and applying the discrete strips under tension to the web of second material.

6. The method of claim 2 wherein the transfer means comprises a rotatable support on which the transfer members are mounted for continuous orbiting along a closed path passing through the supply zone and the transfer zone; and imposing a first orbital radius on the transfer members in the supply zone and imposing a second, different orbital radius on the transfer members in the transfer zone to impart a first linear velocity to transfer members in the supply zone and a second linear velocity to transfer members in the transfer zone.

7. The method of claim 6 including imposing a substantially constant angular velocity on the transfer members.

8. The method of claim 7 including imposing a first orbital radius which is greater than the second orbital radius whereby the linear speed of the transfer means is greater in the supply zone than in the transfer zone.

9. The method of claim 7 including imposing a first orbital radius which is less than the second orbital radius whereby the linear speed of the transfer means is greater in the transfer zone than in the supply zone.

10. The method of claim 2 further including radially pivoting the transfer members to selectively orient the discrete strips relative to the web of second material.

11. The method of claim 2 wherein the first material is selected from the class consisting of elastic materials and materials activatable by one or both of heat and moisture from a substantially non-elastic to an elastic state and the web of second material comprises a material utilizeable in a disposable diaper, and including the additional steps of cutting the web of second material into individual pieces and making disposable garments therefrom.

12. A method of applying discrete strips of a first material in a predetermined pattern to a moving web of a second material comprises:

supplying one or more strips of the first material to a transfer means comprising a rotatable support on which a plurality of transfer members are mounted for continuous orbiting along a closed path passing through a supply zone and a transfer zone, the first material being supplied to the moving transfer members in the supply zone wherein the transfer members carry flexible strip supports on which the discrete strips of first material are removably adhered in a linear configuration;

changing the configuration of the flexible strip supports to a curvilinear configuration while the strips of first material are adhered thereto, thereby correspondingly changing the configuration of the strips of first material prior to transferring them to the web of second material;

cutting the one or more strips of first material to form one or more discrete strips thereof on respective ones of the transfer members;

moving a web of second material concurrently with the the transfer means and into transfer contact therewith in the transfer zone and therein transferring the discrete strips of first material from the transfer means to the moving web of second material; and imposing a first orbital radius on transfer members in the supply zone and a second orbital radius on transfer members in the transfer zone to whereby to impart a first linear velocity to transfer members in the supply zone and a second linear velocity to transfer members in the transfer zone.

13. The method of claim 12 including imposing a substantially constant angular velocity on the transfer members.

14. The method of claim 13 including imposihg a first orbital radius which is greater than the second orbital radius whereby the linear speed of the transfer means is greater in the supply zone than in the transfer zone.

15. The method of claim 13 including imposing a first orbital radius which is less than the second orbital radius whereby the linear speed of the transfer means is greater in the transfer zone than in the supply zone.

16. The method of claim 12 including supplying the first material to the transfer means in the form of one or more continuous strips of material and cutting the first material between the supply zone and the transfer zone to provide the discrete strips.

17. The method of claim 12 wherein the first material comprises an elastic material and including the steps of tensioning the strips and applying the discrete strips under tension to the web of second material.

18. The method of claim 12 further including radially pivoting the transfer members to selectively orient the discrete strips relative to the web of second material.

19. The method of claim 12 wherein the first material is selected from the class consisting of elastic materials and materials activatable by one or both of heat and moisture from a substantially non-elastic to an elastic state and the web of second material comprises a material utilizeable in a disposable diaper, and including the additional steps of cutting the web of second material into individual pieces and making disposable garments therefrom.

* * * * *